United States Patent [19]

Smith

[11] Patent Number: 5,411,019

[45] Date of Patent: May 2, 1995

[54] INTEGRATED OXYGEN RATIO CONTROLLER

[75] Inventor: Jay A. Smith, Harleysville, Pa.

[73] Assignee: North American Drager, Telford, Pa.

[21] Appl. No.: 147,209

[22] Filed: Nov. 3, 1993

[51] Int. Cl.⁶ ............................................. A61M 16/00
[52] U.S. Cl. ............................ 128/203.25; 128/203.14
[58] Field of Search ................... 128/202.22, 203.12, 128/203.14, 203.25

[56] References Cited

U.S. PATENT DOCUMENTS

| | | | |
|---|---|---|---|
| 4,015,617 | 4/1977 | Connolly | 137/88 |
| 4,191,952 | 3/1980 | Schreiber et al. | 340/611 |
| 4,328,823 | 5/1982 | Schreiber | 137/88 |
| 4,442,856 | 4/1984 | Betz | 128/203.14 |
| 5,335,652 | 8/1994 | Falb et al. | 128/203.25 |

Primary Examiner—Edgar S. Burr
Assistant Examiner—Aaron J. Lewis
Attorney, Agent, or Firm—Caesar, Rivise, Bernstein, Cohen & Pokotilow, Ltd.

[57] ABSTRACT

In anesthesia apparatus, an integrated oxygen ratio controller is provided for supplying oxygen and an anesthesia gas through respective flow control valves to a patient breathing circuit. The integrated oxygen ratio controller includes differential pressure sensing means and anesthesia gas flow control means. The differential pressure sensing means includes a rolling diaphragm forming a portion of one wall of a chamber responsive to the pressure in the oxygen pipeline and another rolling diaphragm forming a portion of one wall of another chamber responsive to the pressure in the anesthesia gas pipeline. The anesthesia gas flow control means controls the flow of gas to the anesthesia gas pipeline. The rolling diaphragms are opposed to each other and are coupled together by a displaceable means. The displaceable means is also coupled to the anesthesia gas flow control means to control the flow of anesthesia gas therethrough in response to the differential pressure existing between the pipelines.

13 Claims, 4 Drawing Sheets

INTEGRATED OXYGEN RATIO CONTROLLER

FIELD OF THE INVENTION

This invention relates generally to anesthesia apparatus and, more particularly, to anesthesia gas controllers for anesthesia apparatus.

BACKGROUND OF THE INVENTION

Anesthesia apparatus commercially available commonly include respective flow control valves for controlling the flow or supply of oxygen and anesthesia gas(es), e.g., nitrous oxide, into a common manifold and from there to a patient breathing circuit. Most apparatus also include sensing means and indicating meters, e.g., flow or rotometers, to indicate the gas flow delivered through the flow control valves as well as other system conditions, e.g., gas pressure. The common manifold along with these other sensing means is referred to as the flowmeter assembly.

It is the responsibility of the operator of the anesthesia machine to guarantee that a minimum supply of oxygen is provided in the delivered gas flow. Notwithstanding this responsibility, various accidents have occurred over the past few years when the oxygen percentage decreased below a minimum safety level. Many such accidents have been a result of a failure in the oxygen supply, and inadvertent closing of the oxygen control valve or a misjudgment in the setting of the flows.

Various safety devices are known and commercially available and which respond to the pressure in the oxygen supply line. Such devices signal a decrease or total failure of the oxygen supply pressure. Such devices may also interrupt, or decrease, all gas flows other than oxygen in the event of a partial or total failure of oxygen supply pressure. However, prior art devices which function responsive to oxygen pressure have the major disadvantage that if the oxygen control valve is closed, such that no oxygen is delivered to the patient, the oxygen pressure will still exist in the supply line and the alarm device will not provide an alarm indication even though no oxygen is flowing.

In U.S. Pat. No. 4,191,952 (Schreiber), assigned to the same assignee as this application and whose disclosure is incorporated by reference herein, there is disclosed and claimed a low oxygen flow alarm system for anesthesia apparatus supplying oxygen through one pipeline into a manifold while supplying an anesthesia gas through a second pipeline into the manifold. The alarm system of that invention comprises a first pressure actuated means, e.g., an expandable/contractible chamber having a resilient diaphragm making up a wall of the chamber. The diaphragm is responsive to the oxygen pressure in the first pipeline and has a first output member, e.g., an end portion of a rod connected thereto so that the position of the rod is dependent upon the oxygen pressure. A second pressure actuated means, e.g., an expandable/contractible chamber having a resilient diaphragm making up a wall of the chamber, is also provided. The diaphragm of this chamber is responsive to the anesthesia gas pressure in the second pipeline and is connected to a second output member, e.g., the other end portion of the rod. Thus, the rod's position is dependent upon the anesthesia gas pressure. An alarm means, e.g., a lamp and/or annunciator and an associated switch, are coupled to the rod. The diaphragms act in opposition to each other on the rod. The switch of the alarm means is coupled to the rod to produce an alarm signal whenever the rod has been moved in the second direction to a predetermined position.

In U.S. Pat. No. 4,015,617 (Connolly) there is disclosed anesthesia apparatus providing a mixture of oxygen and nitrous oxide gas into a breathing circuit for the patient. The apparatus includes a flow control valve for adjusting the flow of oxygen into the breathing circuit and a nitrous oxide pressure regulator for regulating the nitrous oxide flow in response to monitored oxygen pressure. By varying the oxygen flow control valve, the flow of nitrous oxide is automatically varied to maintain a predetermined gas flow ratio.

While the device disclosed in the Connolly patent appears suitable for its intended purpose, it nevertheless suffers from at least one major drawback, namely, limited utility. In this regard, the Connolly system does not allow independent adjustment of nitrous oxide and oxygen flow. Thus, if one reduces the oxygen flow in the apparatus of the Connolly patent, the system will automatically make a corresponding reduction in the nitrous oxide flow.

In U.S. Pat. No. 4,328,823 (Schreiber), assigned to the same assignee as this application, and whose disclosure is incorporated by reference herein, there is disclosed and claimed an oxygen flow ratio controller for anesthesia apparatus supplying oxygen through one pipeline into a manifold while supplying an anesthesia gas through a second pipeline into the manifold. Moreover, this controller automatically regulates the ratio of oxygen gas to anesthesia gas provided into the patient breathing circuit while enabling independent control of oxygen and anesthesia gas so long as a threshold concentration of oxygen exists. This threshold concentration of oxygen is reflected by a critical oxygen gas to anesthesia gas ratio value, hereinafter known as the predetermined minimum threshold level. In particular, the controller comprises a flow control valve coupled to the second line for controlling the flow of anesthesia gas therethrough. A first expandable/contractible pressure chamber formed partly by a resilient flat diaphragm is provided, responsive to oxygen pressure in the first line. A second expandable/contractible pressure chamber formed partly by a resilient flat diaphragm is provided, responsive to anesthesia gas pressure in the second line. A common rod is connected to each of the diaphragms and to the flow valve. The diaphragms act in opposition to each other to move the rod and operate the flow control valve in response to the differential pressure monitored by the chambers.

The assignee of this application, N.A.D., Inc., has been selling a controller, referred to hereinafter as the ORMC (Oxygen Ratio Monitor Controller), which incorporates many of the features of U.S. Pat. No. 4,328,823. In addition, the ORMC operates as discussed below.

For high fresh gas (oxygen gas and anesthesia gas) flow rates (e.g., 2 liters/minute and greater) to the ORMC, the predetermined minimum threshold level remains constant (e.g., 25 percent). Under normal operating conditions, the ratio of oxygen gas to anesthesia gas is well above the predetermined minimum threshold level. Should the ratio of oxygen gas to anesthesia gas begin to fall toward the predetermined minimum threshold level, the flow control valve responds by restricting the flow of anesthesia gas, thereby establishing a new ratio that exceeds the predetermined minimum threshold level. In particular, under these conditions, the valve does not close. Instead, the valve is continuously being positioned to reflect the particular oxygen gas to anesthesia gas ratio, restricting the flow of anesthesia gas when the ratio approaches the predetermined minimum threshold level, and thereby correcting the flow of anesthesia gas to establish a new ratio above the predetermined minimum threshold level. However, in the unusual circumstance where the oxygen flow is accidentally cut off, the flow control valve would close.

For low fresh gas flow rates (e.g., less than 2 liters/minute), it is necessary to ensure that even greater concentrations of oxygen are being supplied to the patient. This is accomplished by providing for increased predetermined minimum threshold levels (well above 25 percent) for decreasing fresh gas flow rates. In other words, as the fresh gas flow rate decreases, the ORMC requires increasingly higher percentages of oxygen in the mixture than at the high flow gas rates or else the flow control valve begins to restrict the flow of anesthesia gas.

However, the ORMC requires a dynamic seal (formed by the rod passing through an O-ring) between the flow control means and the second pressure chamber. This arrangement introduces friction and hysteresis into the system. In addition, should this dynamic seal ever fail, or if a leak should occur, the control valve could send uncontrolled amounts of anesthesia gas into the patient breathing circuit. Moreover, the adjustment of the ORMC predetermined minimum threshold level for low fresh gas flow rates is a "trial and error" method: an integral adjustment mechanism is adjusted either at the factory or by a field service technician. This must be followed by connecting the adjusted ORMC to a test assembly for determining if the correct adjustment was made. If it was not correctly adjusted, the method must be repeated. Furthermore, the large size of the ORMC requires that it be remotely located, requiring substantial external pneumatic lines connected between it and the anesthesia apparatus. Finally, the flat diaphragms used in the ORMC's first and second pressure chambers are subject to stretching and stressing which may cause the ORMC operation to drift, i.e., as the diaphragms stretch, the ratio of oxygen gas to anesthesia gas at which the flow control valve closes drifts away from the predetermined minimum threshold level, requiring adjustment by a field service technician.

OBJECTS OF THE INVENTION

It is yet another object of this invention to eliminate the dynamic seal between the output chamber and the anesthesia monitoring unit pressure chamber of the ORMC.

Accordingly, it is the general object of this invention to provide a controller which overcomes the disadvantages of the prior art.

It is a further object of this invention to provide an oxygen ratio controller apparatus for an anesthesia machine and which includes a safer and more reliable flow control valve.

It is yet another object of this invention to provide an oxygen ratio controller for an anesthesia machine having expandable/contractible chambers formed of diaphragms which are resistant to stretch induced failure.

It is still a further object of this invention to provide an oxygen ratio controller for an anesthesia machine which provides for the incremental adjustment of the predetermined minimum threshold level for low fresh gas flow rates.

It is still yet a further object of this invention to provide an oxygen ratio controller that contains fewer piece parts, its total material cost is significantly less than the ORMC, and is smaller in size.

It is yet a further object of this invention to provide an oxygen ratio controller that can be directly connected to the flowmeter assembly of an anesthesia machine, eliminating the need to run copper tubing to a remote location and reducing the troubleshooting time by having the integrated oxygen ratio controller be a functional subassembly of the flowmeter assembly.

SUMMARY OF THE INVENTION

These and other objects of the instant invention are achieved by providing a gas control system for use with an anesthesia apparatus which supplies oxygen through one line into a manifold while supplying an anesthesia gas through a second line into the manifold. The first line includes a first adjustable means, e.g., an oxygen flow control valve, for enabling the adjustment of the flow of oxygen through the first line in a first direction from upstream to downstream. The second line includes a second adjustable means, e.g., an anesthesia gas flow control valve, for enabling the adjustment of the flow of anesthesia gas through the second line in the first direction. The first and second adjustable means are adjustable independently of each other.

The gas control system additionally comprises differential pressure sensing means and a flow control means. The flow control means is coupled to the second line downstream of the second adjustable means in order to control the flow of anesthesia gas through the second line. The flow control means itself comprises valve means, e.g., a spring biased valve, and plunger means coupled to the valve means.

The differential pressure sensing means comprises a first expandable/contractible chamber, e.g., a chamber having a portion of a wall formed of a diaphragm, which is responsive to oxygen pressure in the first line. A second expandable/contractible chamber, e.g., a chamber having a portion of a wall formed of a diaphragm, is provided responsive to anesthesia gas pressure in the second line. Displaceable means, e.g., a common rod, is provided coupled between the first expandable/contractible chamber and the second expandable/contractible chamber, and coupled to the plunger means for controlling the valve means.

The displaceable means is movable, e.g., reciprocable, in response to a differential pressure exhibited between the first and second expandable/contractible chambers, whereupon if the ratio of the flow of oxygen to the flow of anesthesia gas is above a predetermined minimum threshold level, the differential pressure causes the displaceable means to move toward a first position that opens the valve means, thereby permitting the flow of anesthesia gas into the manifold in the ratio established by the first and second adjustable means. Whenever the ratio of the flow of oxygen to the flow of anesthesia gas falls toward the predetermined minimum threshold level, the differential pressure causes the displaceable means to move to an intermediate position that causes the valve means to maintain the ratio of the flow of oxygen to the flow of anesthesia gas above the predetermined minimum threshold level. Whenever the flow of oxygen is cut off, the differential pressure causes the displaceable means to move to a second position, closing the valve means, thereby stopping the flow of anesthesia gas into the manifold.

DESCRIPTION OF THE DRAWINGS

Other objects and many of the attendant advantages of this invention will be readily appreciated as the same becomes better understood by reference to the following detailed description when considered in connection with the accompanying drawings wherein.

DESCRIPTION OF THE PREFERRED EMBODIMENT OF THE INVENTION

Figure 1:
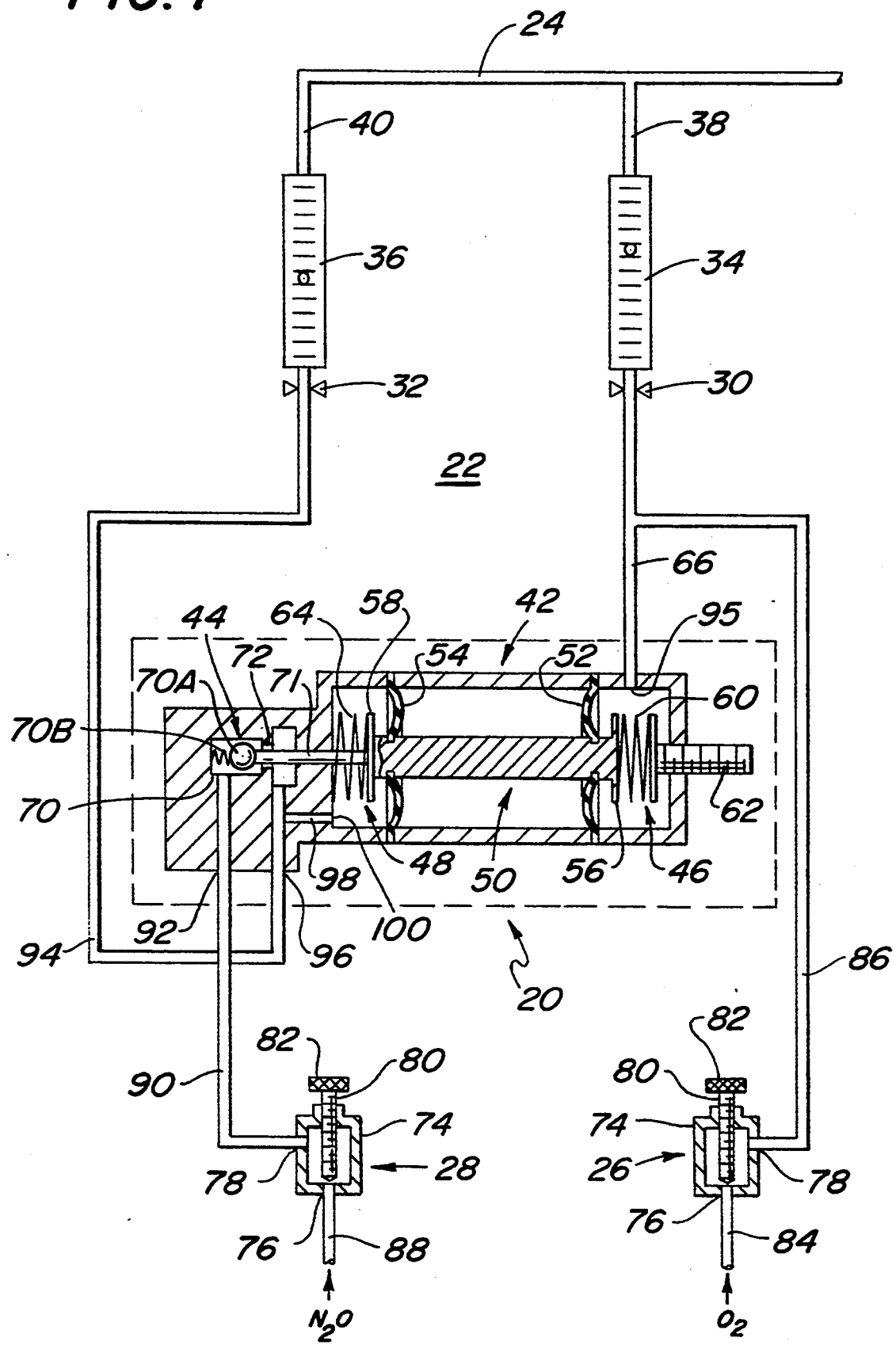
FIG. 1 is a schematic diagram of a portion of a conventional anesthesia apparatus having flow meters and including an integrated oxygen ratio controller constructed in accordance with this invention.

Referring now in greater detail to the various figures of the drawing wherein like reference characters refer to like parts, there is shown generally at 20 in FIG. 1 an integrated oxygen ratio controller constructed in accordance with this invention coupled to a conventional anesthesia apparatus or machine 22 (of which only the flowmeter assembly portion is shown and described herein). The anesthesia machine 22 being of conventional construction is arranged to provide a mixture of oxygen and anesthesia gas(es) through a manifold 24 for inhalation by the patient. To that end, the machine 22 basically comprises a compressed oxygen cylinder (not shown) and a compressed anesthesia gas cylinder (not shown). Oxygen and the anesthesia gas, e.g., nitrous oxide, are provided via respective flow control valves 26 and 28, respective restrictors 30 and 32, and respective flow meters 34 and 36 into the common manifold 24 where the gases mix for supply to the patient breathing circuit (not shown). The flow control valves 26 and 28 are manually adjustable to establish the rate of flow of gas therethrough. Each restrictor is a sintered metal, linear restrictor.

Each of the flow meters 34 and 36 is of conventional construction to indicate the rate of gas flow into the manifold and comprises a tapered glass tube having a gradually increasing inside diameter in the upward direction. The glass tube contains a free-moving float which serves as an indicator of the rate of gas flow through the tube. The tube is graduated in terms of volume per unit time. The upper end of flow meter 34 is connected to a branch pipeline 38 which forms the oxygen input to the common manifold 24. The upper end of flow meter 36 is connected to a branch pipeline 40 which forms the anesthesia gas input to the common manifold 24.

The integrated oxygen ratio controller 20 of this invention is arranged to control or regulate the percentage of oxygen in the oxygen-nitrous oxide mixture. The operation of the controller 20 is similar to that of the ORMC, in particular, the operation at high fresh gas flow rates and at low fresh gas flow rates, as described earlier. The oxygen concentration is monitored by comparing the ratio of the oxygen flow to the nitrous oxide flow provided into the fresh gas manifold 24. This is accomplished by comparing the oxygen pressure and the nitrous oxide pressure that result from the flow of such gases through restrictors 30 and 32, respectively. As will be appreciated by those skilled in the art, the resulting pressures within the housings of valves 26 and 28 are each a function of the resistance of the associated restrictor and the gas flow through the restrictor. In general, this relationship is not linear, but an increase in flow always produces an increase in pressure. Consequently, the ratio of oxygen pressure to the nitrous oxide pressure is related to the oxygen concentration in the manifold 24.

The integrated oxygen ratio controller 20 basically comprises differential pressure sensing means 42 and flow control means 44. The differential pressure sensing means 42 monitors the pressure ratio by comparing the oxygen pressure resulting from the flow of oxygen through oxygen restrictor 30 to the nitrous oxide pressure resulting from the flow of nitrous oxide through the nitrous oxide restrictor 32. The flow control means 44 is in the form of a valve (to be described later), driven by a plunger (also to be described later) under the control of the differential pressure sensing means 42. The valve is arranged to restrict the flow of nitrous oxide if the ratio of oxygen flow to the nitrous oxide flow falls toward the predetermined minimum threshold level and thereby re-establish a new oxygen gas to anesthesia gas ratio that is above the predetermined minimum threshold level, resulting in a safe concentration of nitrous oxide flow.

The differential pressure sensing means 42 basically comprises a first pressure chamber 46 that is expandable and contractible, a second pressure chamber 48 that is expandable and contractible, and a displaceable means 50. The first pressure chamber 46 monitors the oxygen flow to the anesthesia apparatus 22 and the second pressure chamber 48 monitors the anesthesia gas flow to the anesthesia apparatus 22. The first chamber 46 (hereinafter, the "oxygen pressure chamber") includes a diaphragm 52 (to be described later) which forms a portion of a wall of the chamber 46 while the second chamber 48 (hereinafter, the "nitrous oxide pressure chamber") includes a diaphragm 54 (to be described later) which forms a portion of a wall of the chamber 48. The displaceable means 50 is disposed between the diaphragm 52 and the diaphragm 54 such that a clamp member 56 (to be described later) forming one end of the of the displaceable means 50 projects through the diaphragm 52 and into the oxygen pressure chamber 46 and another clamp member 58 (to be described later) forming the other end of the displaceable means 50 projects through the diaphragm 54 and into the nitrous oxide pressure chamber 48. The displaceable means 50 is arranged to be reciprocated longitudinally, i.e., from right to left (and vice versa) in response to the existing differential pressure as monitored by the differential pressure sensing means 42 so that its longitudinal position is indicative of the existing differential pressure and concomitant gas flow rates.

A biasing spring 60 is provided in the oxygen pressure chamber 46 coupled between the end 56 of the displaceable means 50 and an external adjustment screw 62. A similar biasing spring 64 is provided in the nitrous oxide pressure chamber 48 coupled between the other end 58 of the displaceable means 50 and a fixed end wall of the nitrous oxide pressure chamber 48. The combination of biasing springs 60 and 64 and the adjustment screw 62 permit the predetermined minimum threshold level to be incrementally adjusted for low fresh gas flow rates, if necessary, to meet operating specifications.

The oxygen pressure chamber 46 is pressurized via a pilot pipeline 66 from the oxygen flow control valve 26. That valve 26 is located upstream of the oxygen restrictor 30. The nitrous oxide pressure chamber 48 is pressurized via the flow control means 44 from a valve outlet pipeline 90 from the anesthesia flow control valve 28, depending on the condition of the flow control means 44. As will be described in detail later, whenever the flow control means 44 is open, the nitrous oxide pressure chamber 48 will be in fluid communication with the pipeline 90 so that the pressure within the chamber 48 is the same as in an outlet pipeline 94.

As depicted in FIG. 1, expansion or contraction of the oxygen pressure chamber 46 will correspondingly move the end 56 of the displaceable means 50 to the left or to the right, respectively. Similarly, expansion or contraction of the nitrous oxide pressure chamber 48 will correspondingly move the end 58 of the displaceable means 50 to the right or to the left, respectively. Hence, the expansion/contraction of the chambers 46 and 48 work in opposition to one another, with the displaceable means 50 moving in the direction of the expansion of the chamber 46 or 48 experiencing the greater pressure.

The flow control means 44 basically comprises a ball valve 70 and plunger means 71 (to be described later). The ball valve 70 includes a ball 70A, a helical spring 70B, and a valve seat 72 disposed in the path of the flow of the nitrous oxide gas. When the ball 70A is maximally displaced from the valve seat 72 (where the oxygen gas to anesthesia gas ratio is well above the predetermined minimum threshold level), nitrous oxide gas flows, unrestricted by the ball valve 70, from the nitrous oxide cylinder (not shown) through the valve 28, the line 90, the valve 70, the output pipeline 94 (to be described later), the restrictor 32, the flow meter 36 and the branch pipe 40 to the common manifold 24. If the ball 70A is ever seated in the valve seat 72, all nitrous oxide flow through the valve 70 is stopped. For any intermediate position between the maximally displaced position of the ball 70A and the closed position, the ball 70A and seat 72 act to regulate the flow of nitrous oxide gas.

The differential pressure sensing means 42 drives the plunger means 71. The plunger means 71 comprises a rod and stop (to be described later) which are interposed between the displaceable means 50 and the ball valve's ball 70A. The plunger means 71 is arranged to be reciprocated longitudinally, i.e., from right to left (and vice versa) by the displaceable means 50. The longitudinal position of the plunger means 71 establishes whether the flow control ball valve 70 is open, closed, or somewhere in between. Basically, the plunger means 71, under the control of the displaceable means 50, provides a counteracting force to the ball spring 70B which tends to seat the ball 70A in the valve seat 72.

One of the distinguishing features of the integrated oxygen ratio controller 20 over the ORMC is the location of the flow control means 44. In the present invention, the flow control means 44 is located downstream of the nitrous oxide flow valve 28, thereby simplifying the flow control means 44 by eliminating the need to feedback the control valve 28 pressure through a pilot pipeline (as is necessary in the ORMC) and also by eliminating the need to isolate the nitrous oxide pressure chamber 48 from the flow control means 44 (as is also necessary in the ORMC).

The flow of oxygen and nitrous oxide gas to the integrated oxygen ratio controller 20 will now be discussed. The flow valves 26 and 28 are each of conventional construction and each includes a housing 74 having a gas inlet port 76, a gas outlet port 78, and an adjustable needle valve element 80. A knob 82 is connected to the element 80 of valve 26 for adjusting the rate of oxygen flow through the valve. A similar knob 82 is connected to the needle element 80 of valve 28 for adjusting the nitrous oxide flow therethrough. A valve inlet pipeline 84 is connected to a port 76 of the valve 26 to carry oxygen from a storage tank (not shown) to the valve for distribution to its outlet port 78. A valve outlet pipeline 86 is connected between the outlet port 78 and the oxygen restrictor 30. A pilot pipeline 66 is connected between the valve outlet pipeline 86 and the oxygen pressure chamber 46.

The inlet port 76 of the flow control valve 28 is connected to a valve inlet pipeline 88, providing the nitrous oxide gas from its storage tank (not shown) to the valve 28. The valve outlet pipeline 90 is connected between the outlet port 78 of the valve 28 and an inlet port 92 of the flow control means 44. The outlet pipeline 94 is connected between the outlet port 96 of the flow control means 44 and the nitrous oxide restrictor 32.

As mentioned heretofore, the pressure ratio is monitored by the differential pressure sensing means 42. The sensing means 42 is in the form of the heretofore identified two expandable/contractible chambers 46 and 48. The oxygen pressure chamber 46 basically comprises a pressure chamber having a diaphragm 52 which forms a portion of a wall of the chamber 46. The oxygen pressure chamber 46 includes a pilot port 95 to which the pilot pipeline 66 is connected and which is in communication with chamber 46. The nitrous oxide pressure chamber 48 basically comprises a pressure chamber having a diaphragm 54 which forms a portion of a wall of the chamber 48. Each diaphragm 52 and 54 is a "rolling diaphragm" for reasons to be discussed later. Each diaphragm is coupled to a respective end of the displaceable means 50 such that when each chamber 46 and 48 expands or contracts, thereby moving the displaceable means 50, only certain portions of each diaphragm "roll" or "bend" to allow movement of the displaceable means 50 while maintaining the tight seal of each pressure chamber.

As discussed previously, the location of the flow control means 44 eliminates the need to isolate the nitrous oxide pressure chamber 48 from the valve 70. Therefore, there is no need for a dynamic seal between the flow control valve 70 and the pressure chamber 48. However, one advantage of having a dynamic seal is that it introduces some friction and concomitant damping of the system. Such damping is necessary since the displaceable means 50 (and, therefore, the plunger means 71 and ball valve 70) is continuously repositioned at a location corresponding to the particular oxygen gas to anesthesia gas ratio. In the present controller 20, where there is no dynamic seal, the absence of friction could potentially set up a resonance condition. To prevent this action, damping is incorporated into the controller 20 by way of a controlled impedance flow restrictor 98. The damping introduced by the restrictor 98 eliminates resonance without introducing hysteresis into the controller 20 under steady state conditions. In particular, the restrictor 98 provides a passageway within the housing containing the flow control means 44 and wherein the restrictor 98 is interposed between the outlet port 96 and a pressure sensing port 100. The pressure sensing port 100 is in communication with the interior of the nitrous oxide pressure chamber 48. Thus, the restrictor 98 communicates the pressure of the nitrous oxide gas flow in line 94 to the nitrous oxide pressure chamber 48 as the nitrous oxide prepares to exit the outlet port 96.

Figure 2:
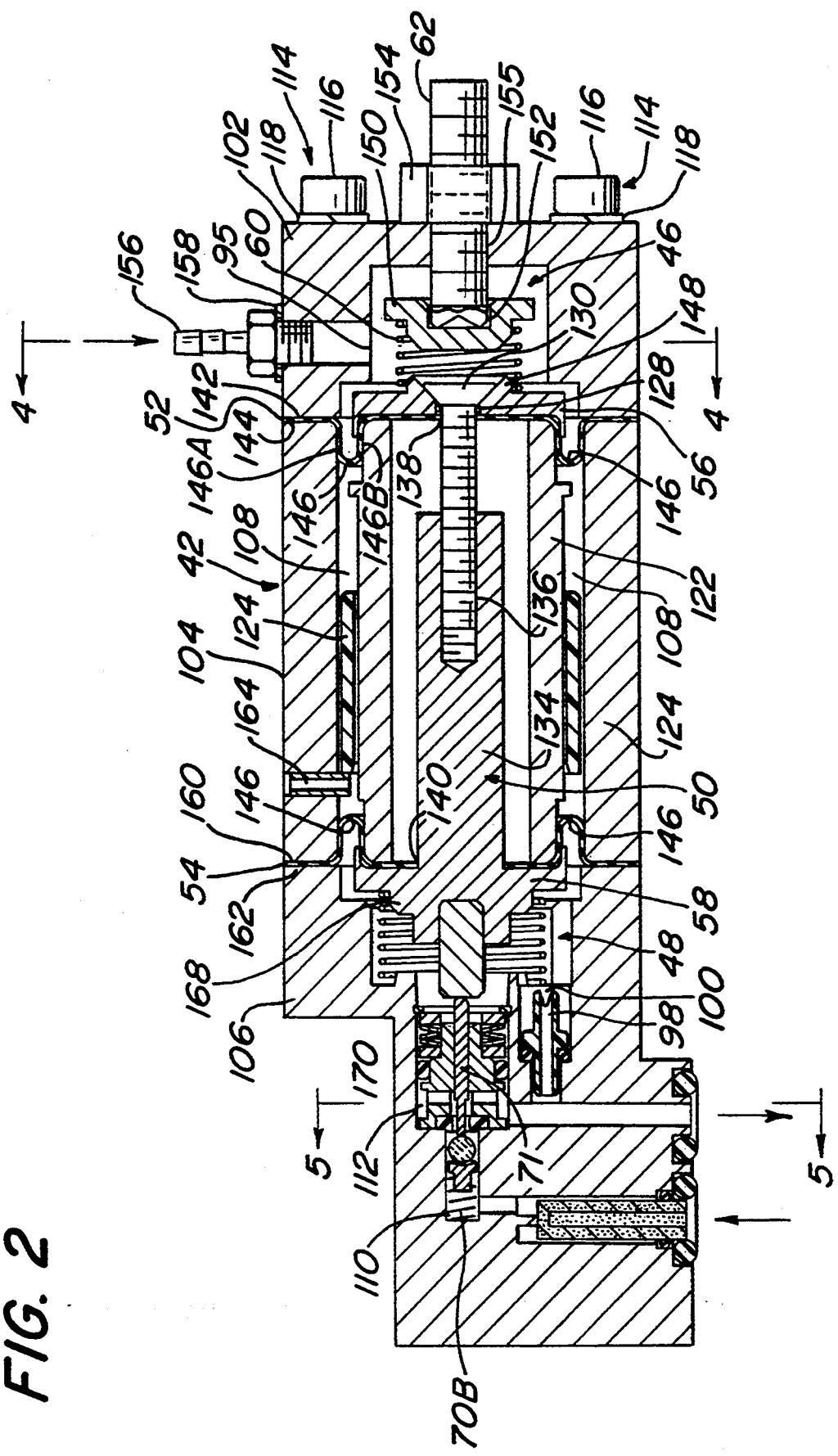
FIG. 2 is a vertical sectional view showing the details of the integrated oxygen ratio controller of the present invention.
Figure 3:
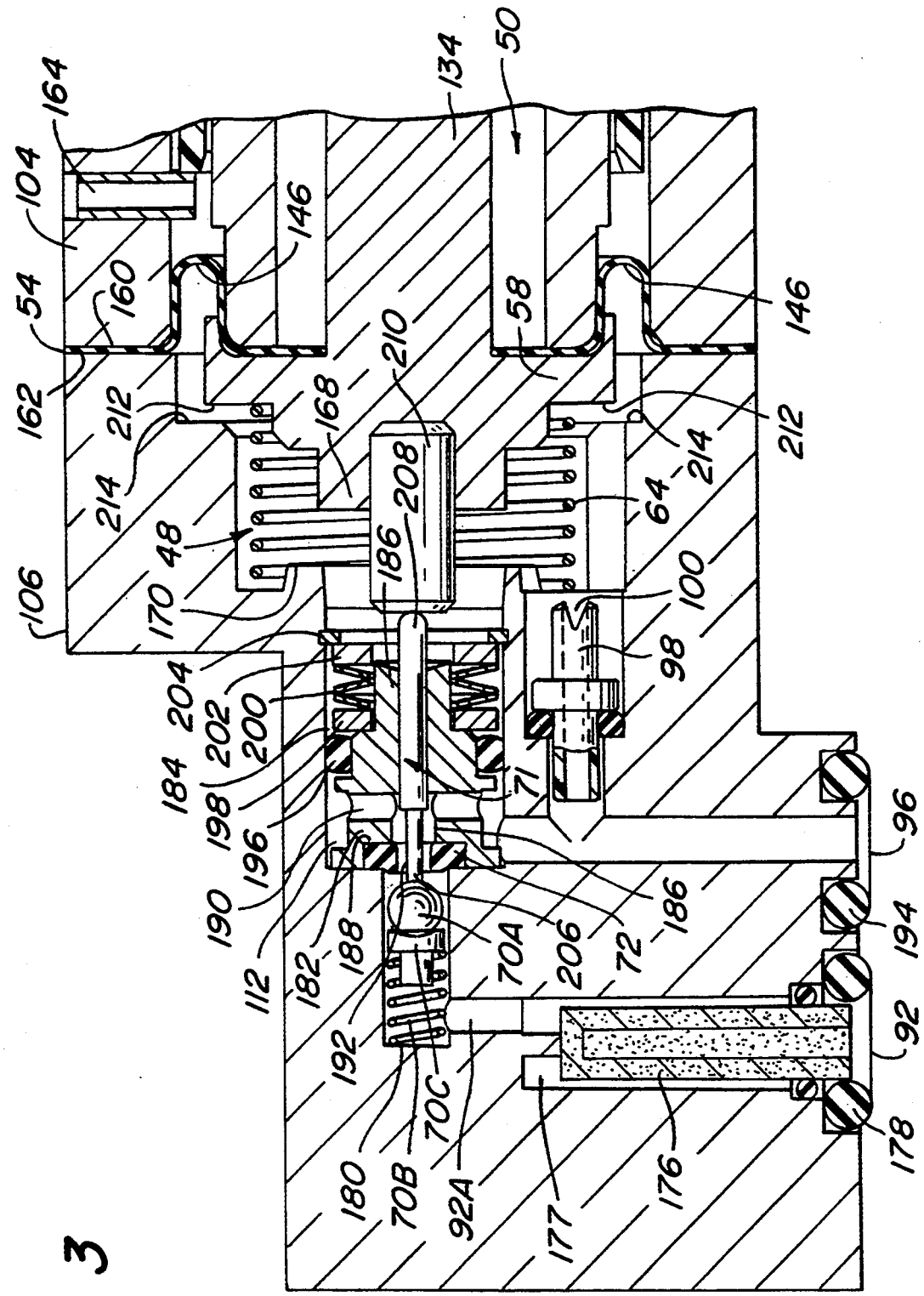
FIG. 3 is an enlarged vertical sectional view of a portion of the controller shown in FIG. 2 to better show the details of the components therein.

Referring now to FIGS. 2 and 3, the details of the controller 20 will now be discussed. As can be seen therein, the controller 20 comprises three housing sections: a right housing section 102, a middle housing section 104 and a left housing section 106. The right housing section 102 has a hollow interior which forms a portion of the oxygen pressure chamber 46. The middle housing section 104 has a hollow interior 108 through which the displaceable means 50 moves. The left housing section 106 has a hollow interior which forms a portion of the nitrous oxide pressure chamber 48. The left housing section 106 also includes an input chamber 110 (FIG. 3) and an output chamber 112 (FIG. 3) of the flow control means 44. These chambers will be described later.

Figure 4:
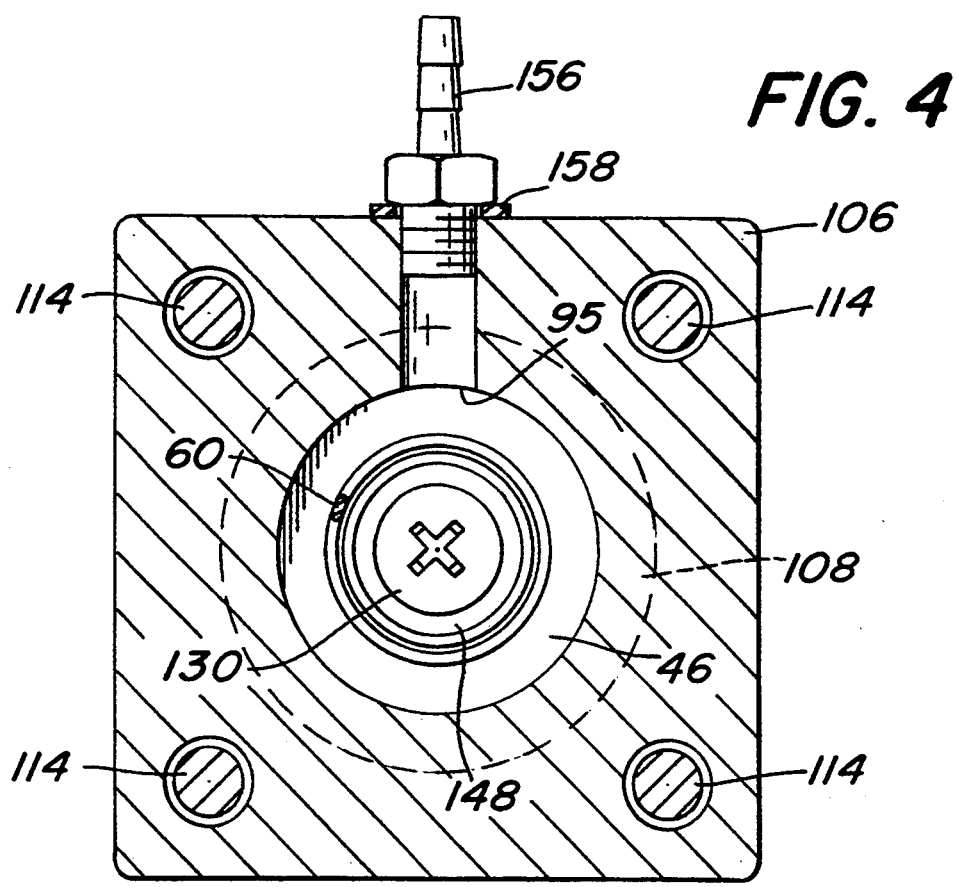
FIG. 4 is an enlarged sectional view taken along line 4—4 of FIG. 2.

The three housing sections 102, 104 and 106 are secured together via four longitudinally extending capped screws 114, only two of which are shown in FIG. 2. Each screw 114 includes a cap or head 116 and a shank (not shown). FIG. 4 shows the location of all four screws 114 in the corners of the three housing sections. Each screw 114 extends through aligned openings in the housing sections 102, 104, and 106 with the shank (not shown) of the screws 114 engaged within a mating threaded opening (not shown) in the housing section 106. The cap 116 of each screw 114 is tightened against a split lock washer 118 and the housing section 102. The housing sections 102, 104 and 106, when secured together, form a common housing for the controller 20. The controller 20 is arranged to be mounted directly on the anesthesia machine 22. In particular, the housing section 106 has a relief area 120 (FIG. 5) that provides clearance for fittings when the integrated oxygen ratio controller 20 is connected to the anesthesia apparatus 22. Although the various figures depict the controller 20 in a horizontal orientation for ease of discussion, the controller 20 is actually mounted in a vertical orientation, with the left housing section 106 being the bottom of the controller 20 and the right housing section 102 being the top of the controller 20.

Before a further description of each of the three housing sections 102, 104 and 106 is made, a description of the displaceable means 50 is necessary. As shown in FIG. 2, the displaceable means 50 basically comprises a piston 122, a bearing sleeve 124, and the previously identified clamp members 56 and 58. The piston 122 comprises a hollow cylinder that fits within the bearing sleeve 124. The sleeve 124 maintains the alignment of the piston 122 within the hollow interior 108 of the middle housing section 104. The right end clamp 56 is a disk-like member which has a hole 128 for receiving a flathead screw 130. The left end clamp 58 is also a disk-like member which has a central shaft 134 projecting therefrom and is disposed within the hollow cylinder of the piston 122. The central shaft 134 has a threaded bore 136 for receipt of the shank of the flathead screw 130. The diaphragm 52 has a hole 138 within its central portion to allow passage of the flathead screw 130 therethrough. The diaphragm 54 has a hole 140 within its central portion to allow passage of the central shaft 134 of the clamp 58 therethrough. The diaphragms 52 and 54 are coupled to the displaceable means 50 as follows: The central portion of the diaphragm 52 is trapped between the right clamp 56 and one end of the piston 122. The central portion of the diaphragm 54 is trapped between the left clamp 58 and the other end of the piston 122. The components making up the displaceable means 50 are held together when the flathead screw 130 is screwed into the threaded bore 136 in the shaft 134, since this pulls the clamps, 56 and 58, together interposing the piston 122 tightly therebetween. The resulting arrangement effectively ties the diaphragms 52 and 54 together. The clamp 56 and the diaphragm 52 form one wall of the oxygen pressure chamber 46, while the clamp 58 and the diaphragm 54 form one wall of the nitrous oxide pressure chamber 48. Oxygen pressure and nitrous oxide pressure are exerted against the walls of these chambers, respectively. The respective wall of each chamber formed by the clamp and diaphragm is movable depending on the respective pressure exerted against the respective wall. The resulting movement of these respective walls give rise to the motion of the displaceable means 50.

The right housing section 102 has an end surface 142 and the middle housing section 104 has an end surface 144. The two surfaces abut when the sections are secured together. The diaphragm 52 is of a truncated-cone form, consisting of a resilient material, e.g., rubber, and whose periphery is interposed and tightly held between the surfaces 142 and 144 when the housing sections 102 and 104 are secured together.

As discussed earlier, the diaphragm 52 is a rolling diaphragm. As can be seen in FIG. 2, when the rolling diaphragm 52 is installed into the controller 20, the truncated-cone form of the diaphragm 52 is compressed by the piston 122 to form an annular portion 146 that is looped and interposed between the outer surface of the piston 122 and the circular inner surface of the housing section 104. When oxygen pressure in the oxygen pressure chamber 46 pushes the clamp 56 to the left, it causes the displaceable means 50 to move to the left. As the displaceable means 50 moves to the left, the annular portion 146 of the diaphragm 52 "rolls" or "bends" to permit the displaceable means 50 to move while maintaining a tight seal of the oxygen pressure chamber 46. An example of the rolling action can be seen in FIG. 2. When the clamp 56 is pushed to the left, loop portion 146A lengthens while loop portion 146B shortens to accommodate movement of the displaceable means 50 to the left. The opposite occurs when the displaceable means 50 moves to the right. This rolling or bending action of the diaphragm 52 has no stretching component as do the flat diaphragms used in the ORMC. Hence, the rolling diaphragms used in the present invention are immune to the effects of diaphragm stretching, making the system more stable. The diaphragm 54 is similarly constructed to diaphragm 52 and operates in the same manner. Thus, the middle housing 104 has an end surface 160 and the left housing section 106 has an end surface 162. The two surfaces abut when the sections are secured together. The periphery of the diaphragm 54 is interposed and tightly held between the surfaces 160 and 162 when the sections 104 and 106 are secured together. Therefore, if the nitrous oxide pressure chamber 48 experiences nitrous oxide gas pressure that would push the clamp 58 to the right, thereby moving the displaceable means 50 to the right, the annular portion 146 of diaphragm 54 will "roll" along the surfaces of the piston 122 and the housing section 104 to accommodate this displacement.

As can be seen in FIG. 2, the right biasing spring 60 and the right clamp 56 are located within the oxygen pressure chamber 46. The clamp 56 includes a raised central boss 148 in which the heretofore identified hole 128 is located. The boss 148 serves to hold the spring 60 in place to that end. One end of the spring 60 fits around the boss 148 while the other end of the spring 60 is disposed about a spring retainer 150. The spring retainer 150 has a seat 152 that receives the tip of the adjustment screw 62. The other end of the adjustment screw 62 projects out of the right housing section 102 and is secured to the housing 102 by way of a sealing jam nut 154 and a threaded hole 155 in the housing 102. The sealing jam nut 154 includes an elastomer ring (not shown) that is trapped between the jam nut 154 and the outer surface of the right housing section 102 to prevent leakage. None of these components interferes with the oxygen pressure being sensed within the oxygen pressure chamber 46 since these components are centralized within the chamber 46 as can be seen in FIG. 4. Oxygen pressurizes the chamber 46 through the pilot port 95 via a straight fitting 156. The fitting 156 is directly coupled to the pilot pipeline 66. The fitting 156 is tightened against the right housing section 102 by way of a washer 158 (FIG. 4).

As can be seen in FIG. 2, the looped portions 146 of the diaphragms 52 and 54 seal off the hollow interior 108 of the middle housing section 104 from the pressure chambers 46 and 48. A vent 164 is provided in the middle housing section 104 in communication with the interior 108 and the ambient atmosphere. Should either diaphragm 52 or 54 rupture or leak, the escaping gas will "bleed" thorough the interior 108 and the vent 164 to the ambient atmosphere rather than mixing with, or leaking into, the other pressure chamber. In addition, the piston 122 has its own vent (not shown) comprising a hole through the piston wall that provides a passageway for any internal leaks of anesthesia gas or oxygen gas that may find their way into the area surrounding the shaft 134. Should such a leak occur, the leaking gas would pass through the piston vent (not shown), the interior 108 and then out through the housing vent 164.

The left housing section 106 serves to contain the nitrous oxide pressure chamber 48 and the flow control means 44. Thus, as can be seen in FIG. 2, the spring 64 and the left clamp 58 project into the nitrous oxide pressure chamber 48. In particular, the left clamp 58 has a raised boss 168 about which one end of the spring 64 is disposed. The other end of the biasing spring 64 is seated around an internal chamber flange 170 inside the nitrous oxide pressure chamber 48. None of these components interferes with the nitrous oxide gas pressure being sensed within the nitrous oxide pressure chamber 48 since these components are centralized within the chamber 48.

Unlike the oxygen pressure chamber 46 which is subjected to oxygen pressure directly from its corresponding flow control valve 26, the anesthesia gas pressure must first pass through the flow control means 44 before it pressurizes the nitrous oxide pressure chamber 48.

The flow control means 44 basically comprises the heretofore identified input chamber 110, output chamber 112, valve ball 70A, helical spring 70B, valve seat 72 and plunger means 71. Additionally, the flow control means comprises a ball retainer 70C. This retainer 70C is interposed between one end of the helical spring 70B and the ball 70A. This retainer 70C serves to keep the ball 70A generally centered with respect to the valve seat 72. Referring to FIG. 3, an enlargement of the internal portions of the left housing section 106 showing the nitrous oxide pressure chamber 48 and the flow control means 44 can be seen. As can be seen therein, the output chamber 112 is simply an extension of the chamber 48, but only a portion of the output chamber (to be described later) is in fluid communication therewith.

The valve 70 is located within the input chamber 110. In particular, the chamber 110 comprises a cylindrical bore with the helical spring 70B interposed between an end wall 180 of the input chamber 110 and the ball retainer 70C. The ball retainer 70C includes a concave recess to receive a portion of the ball 70A therein. The diameter of the input chamber 110 is slightly greater than the diameter of the valve ball 70A to enable the ball 70A to move longitudinally therein. The helical spring 70B and the ball retainer 70C tend to bias the ball 70A fully into the valve seat 72. On the other hand, the plunger means 71, under the control of the displaceable means 50, acts in opposition to this spring 70B by displacing the ball 70A off of the valve seat 72.

The inlet port 92 of flow control means 44 is in the form of a bore which extends into the body of the left housing section 106. The port 92 communicates with the input chamber 110 through a narrower bore 92A. A filter 176, to trap any foreign matter within the nitrous oxide as it enters the flow control means 44, is disposed within the bore forming the port 92. A boss 177 maintains the position of the filter 176 away from the opening to the narrower bore 92A. An O-ring 178 is provided at the opening to inlet port 92 to ensure that the connection of the line 90 thereto does not leak nitrous oxide. This O-ring 178 has an inner diameter which forms an interference fit around the opening of the filter 176.

Figure 5:
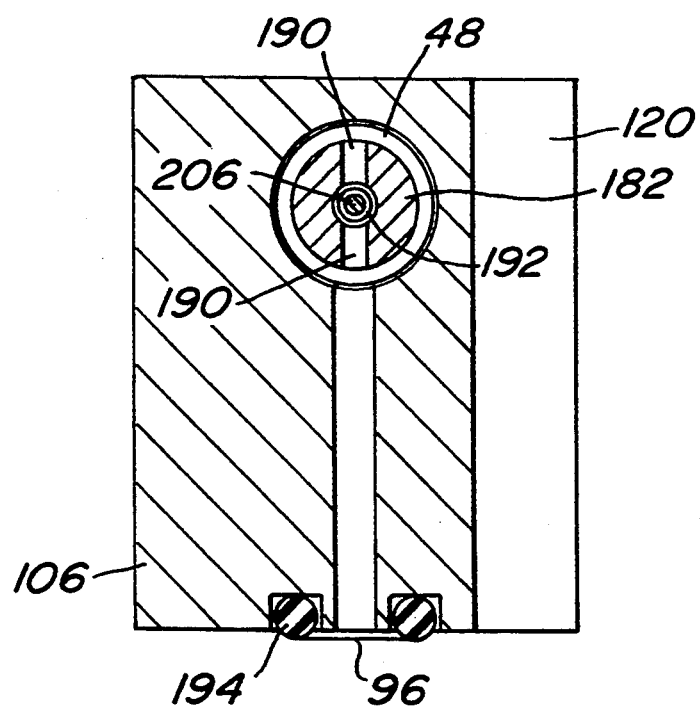
FIG. 5 is an enlarged sectional view taken along line 5—5 of FIG. 2.

The valve seat 72 is mounted in abutment with the front edge of the input chamber 110 and is held in place via a retainer 182 (FIGS. 3 and 5). The retainer 182 is held within the bore forming the output chamber 112 in the left housing section 106. The retainer 182 includes a central passageway 186 extending therethrough and terminating at one end in an annular recess 188 in which the valve seat 72 is located. The retainer 182 is of smaller outside diameter adjacent the valve seat 72 than the bore in which it is located to form the output chamber 112 therebetween. Two radially extending openings 190 are provided in the retainer 182 in communication between the annular output chamber 112 and the central passageway 186, as can be seen in the cross-sectional view in FIG. 5. The valve seat 72 includes a central opening 192 which communicates with the output chamber 112 and with the two radially extending openings 190.

The outlet port 96 of the flow control means 44 extends into the body of the left housing section 106, and communicates with the output chamber 112. An O-ring 194 is provided at the outlet port 96 to form a seal to prevent leakage of the nitrous oxide when the line 94 is connected to the port 96. The inner diameter of this O-ring 194 forms an interference fit around the periphery of the port 96. An O-ring 196 is attached to the periphery of the central portion of the retainer 182 whereby this O-ring 196 engages the sides of the bore forming the outer wall of the output chamber 112, thereby sealing off a portion of the output chamber 112 from the interior of the nitrous oxide chamber 48. A bore designated by the reference number 184 houses the back portion of the retainer 182. A spacer 198, three spring washers 200, another spacer 202 and a retaining ring 204 are also located within the bore 184 and provide the necessary support for aligning the central passageway 186 of the retainer 182 so that the plunger means 71 (to be discussed later) can operate properly.

The plunger means 71 basically comprises a single rod and stop. The rod comprises two portions of different diameters, a plunger pin portion 206 and a plunger dowel portion 208. The plunger stop 210 is fixedly mounted within the raised boss 168 of the left clamp 58. The plunger means 71 is installed within the controller 20 such that the plunger dowel 208 is disposed within the central passageway 186 in the retainer 182, while the plunger pin portion 206 is disposed within the valve seat 72. The plunger stop 210 is arranged to engage the end of the plunger dowel 208 whenever the displaceable means 50 is driven to the left. Movement of the plunger dowel portion 208 to the left drives the plunger pin portion 206 to the left, thereby engaging and displacing the ball 70A away from, and off of, the valve seat 72. Thus, the plunger means acts in opposition to the helical spring 70B which tends to restore the ball 70A into the valve seat 72.

Operation of the controller 20 at high fresh gas flow rates, is as follows: in the event that the ratio of the oxygen flow to the nitrous oxide flow (and consequently the oxygen concentration in the fresh gas provided into the manifold 24) is above the predetermined minimum threshold level, e.g., 25 percent, the force created by the pressure on the clamp 56 within the oxygen pressure chamber 46 exceeds the force created by the pressure on the clamp 58 within the nitrous oxide pressure chamber 48. This causes the clamp 56 to move the piston 122 to the left with the annular portions 146 of the respective rolling diaphragms 52 and 54 rolling or bending accordingly to accommodate the movement to the left. The displaceable means 50, therefore, moves to the left toward a first position. The leftward movement of the piston 122 pushes the plunger stop 210 to the left and into engagement with the plunger means 71 to the left so that the pin 206 contacts the ball 70A to lift the ball 70A from its seat 72 against the bias provided by the helical spring 70B. Accordingly, the nitrous oxide is enabled to flow from the input port 92 and hence to the output port 96 and into the restrictor 32.

Under normal operating conditions, at high fresh gas flow rates, the ratio of the oxygen flow to the nitrous oxide flow is well above the predetermined minimum threshold level (e.g., 25 percent). Under those circumstances, the oxygen pressure monitored within the oxygen pressure chamber 46 is so much greater than the nitrous oxide pressure monitored in the nitrous oxide pressure chamber 48 that the displaceable means 50 is maximally displaced to the left such that the left clamp edge 212 contacts the internal stop 214 of the left housing 106 (FIG. 3). This maximally displaced position is heretofore defined as the first position. When the displaceable means 50 is in such position, the plunger means 71 has completely opened the flow control ball valve 70 by counteracting the bias from the helical spring 70B. As long as the displaceable means 50 is on the internal stop 214, the nitrous oxide flow is controlled solely by the nitrous oxide flow control valve 28.

In the event that either or both of the flow control valves 26 and 28 are adjusted so that the ratio of the oxygen flow to the nitrous oxide flow falls toward the predetermined minimum threshold level, the force created by the pressure on the clamp 56 is less than the force created by the pressure on the clamp 58. This causes the clamp 58 to move the piston 122 to the right with the annular portions 146 of the respective rolling diaphragms 52 and 54 rolling or bending accordingly to accommodate the movement to the right. The displaceable means 50, therefore, moves to the right toward an intermediate position. The rightward movement of the piston 122 allows the helical spring 70B to partially overcome the counteracting force provided by the plunger means 71. This reduction in the counteracting force allows the helical spring 70B to push the ball 70A closer to the valve seat 72. However, because the ratio of the oxygen flow to the nitrous oxide flow has not actually dropped to the predetermined minimum threshold level, the displaceable means 50 has not moved far enough to the right to eliminate the entire counteracting force against the helical spring 70B. Therefore, the nitrous oxide gas continues to flow, but the position of the ball 70A restricts the flow of the nitrous oxide to maintain the ratio of the oxygen gas to the anesthesia gas above the predetermined minimum threshold level.

In the event that the flow of oxygen is interrupted such as could occur if the oxygen control valve 26 is accidentally closed, the absence of pressure in the oxygen pressure chamber 46 would permit the pressure in the nitrous oxide chamber 48 to drive the displaceable means 50 to the right, permitting the helical spring 70C to push the ball 70A, unopposed, into the valve seat 72, thereby shutting off the nitrous oxide flow.

The predetermined minimum threshold level can be incrementally adjusted for low fresh gas flow rates by the use of the external adjustment screw 62, whereby a small rotation of the adjustment screw 62 corresponds to an incremental displacement (e.g., thousandths of an inch) of the displaceable means 50. Use of the external adjustment screw is extremely limited in that it is used only at the factory just prior to first use or by a field service technician to maintain the controller 20 to operating specifications. The fine control provided by the external adjustment screw 62 eliminates the "trial and error" method of adjusting the predetermined minimum threshold level for low fresh gas flow rates discussed earlier with regard to the ORMC.

It must be pointed out that small adjustments of the predetermined minimum threshold level are insignificant at high free gas flow rates (e.g., above 2 liters/minute) because the predetermined minimum threshold level is constant for such flow rates. Only at low oxygen flow rates (e.g., less than 2 liters/minute) do the adjustments have any impact.

It must also be pointed out at this juncture that while the device disclosed herein makes use of mechanical means for controlling the flow of nitrous oxide in response to monitored flows of oxygen and nitrous oxide, it is clear that electrical, e.g., solid state, means can be utilized to provide signals indicative of the differential pressure and for opening and closing a nitrous oxide control valve in response to the differential pressure so monitored.

Moreover, the system of the instant invention can with slight modification be used in systems providing more than one anesthesia gas.

As should be apparent from all of the foregoing, the integrated oxygen flow ratio controller of the instant invention is relatively simple in construction, yet offers wide utility since it effects automatic control and regulation of the ratio of oxygen to anesthesia gas provided into the patient breathing circuit, without sacrificing independent control and adjustment of either oxygen or anesthesia gas.

Without further elaboration, the foregoing will so fully illustrate my invention that others may, by applying current or future knowledge, readily adopt the same for use under various conditions of service.

I claim:

1. A gas controller for use with an anesthesia apparatus supplying a flow of oxygen through a first line into a manifold while supplying a flow of anesthesia gas through a second line into the manifold, the first line including first adjustable means for enabling the adjustment of the flow of oxygen through the first line in a first direction from upstream to downstream, the second line including second adjustable means for enabling the adjustment of the flow of anesthesia gas through the second line in the first direction, the first and second adjustable means being adjustable independently of each other, said gas controller comprising:

anesthesia gas flow control means coupled to the second line downstream of the second adjustable means to control the flow of anesthesia gas through the second line, said flow control means comprising valve means and plunger means coupled to said valve means;

differential pressure sensing means comprising a first expandable/contractible chamber responsive to oxygen pressure in the first line, a second expandable/contractible chamber responsive to anesthesia gas pressure in the second line and being coupled to the second line downstream of the second adjustable means, and displaceable means coupled between said first expandable/contractible chamber and said second expandable/contractible chamber, said displaceable means being coupled to said plunger means to control said valve means;

said displaceable means being movable in response to a differential pressure exhibited between said first and second expandable/contractible chambers, whereupon whenever the ratio of the flow of oxygen to the flow of anesthesia gas is above a predetermined minimum threshold level said differential pressure causes said displaceable means to move toward a first position to open said valve means permitting said gasses to flow into said manifold in the ratio established by said first and second adjustable means, whenever the ratio of the flow of oxygen to the flow of anesthesia gas falls toward said predetermined minimum threshold level said differential pressure causes said displaceable means to move to an intermediate position that causes said valve means to maintain said ratio of the flow of oxygen to the flow of anesthesia gas above said predetermined minimum threshold level, and whenever the flow of oxygen is cut off said differential pressure causes said displaceable means to move to a second position, closing said valve means.

2. The gas controller of claim 1 wherein said displaceable means is maximally displaced with said valve means being open when in said first position, said displaceable means being in contact with a mechanical stop when in said first position the flow of anesthesia gas being controlled solely by the second adjustable means whenever said displaceable means is in said first position.

3. The gas controller of claim 1 wherein said predetermined minimum threshold level is fixed over a first range of said flow of oxygen and said flow of anesthesia gas.

4. The gas controller of claim 1 wherein said predetermined minimum threshold level varies over a second range of said flow of oxygen and said flow of anesthesia gas.

5. The gas controller of claim 1 wherein said valve means comprises a ball valve.

6. The gas controller of claim 5 wherein said ball valve is spring biased.

7. The gas controller of claim 1 wherein said displaceable means is longitudinally displaceable, said displaceable means having a first end and a second end.

8. The gas controller of claim 7 wherein said first end is disposed within said first expandable/contractible chamber and said second end is disposed within said second expandable/contractible chamber.

9. The gas controller of claim 7 wherein said differential pressure sensing means further comprises an externally mounted adjustment screw and two biasing springs, said first biasing spring being coupled between said first end of said displaceable means and said externally mounted adjustment screw, said second biasing spring being coupled between said second end of said displaceable means and an adjacent nonmovable surface, said adjustment screw being incrementally adjustable to maintain said predetermined minimum threshold level for low fresh gas flow rates.

10. The gas controller of claim 1 wherein said first expandable/contractible chamber comprises a first rolling diaphragm forming a portion of a wall of said first chamber, said second expandable/contractible chamber comprises a second rolling diaphragm forming a portion of a wall of said second chamber and said displaceable means interconnects said first and second rolling diaphragms and said flow control means, said first and second rolling diaphragms making said system more stable.

11. The gas controller of claim 1 wherein said second expandable/contractible chamber is directly exposed to said flow of anesthesia gas through said valve means.

12. The gas controller of claim 1 comprising a controlled impedance restrictor through which said flow of anesthesia gas passes for direct exposure to said second expandable/contractible chamber responsive to anesthesia gas in said second line, said controlled impedance flow restrictor providing damping.

13. The gas controller of claim 1 wherein said system is housed within a compact housing arranged to be mounted to said anesthesia apparatus utilizing short length pneumatic lines.

* * * * *